(12) United States Patent
Frigg et al.

(10) Patent No.: US 9,295,503 B2
(45) Date of Patent: Mar. 29, 2016

(54) DEVICE FOR BONE FIXATION WITH AT LEAST ONE THROUGH HOLE

(75) Inventors: Robert Frigg, Bettlach (CH); Marcel Fuhrer, Frauenfeld (CH); Stephan Küppers, Derendingen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1494 days.

(21) Appl. No.: 12/090,920

(22) PCT Filed: Nov. 16, 2005

(86) PCT No.: PCT/CH2005/000680
§ 371 (c)(1),
(2), (4) Date: Sep. 8, 2008

(87) PCT Pub. No.: WO2007/056874
PCT Pub. Date: May 24, 2007

(65) Prior Publication Data
US 2009/0222049 A1    Sep. 3, 2009

(51) Int. Cl.
A61B 17/80 (2006.01)
A61B 17/72 (2006.01)
A61B 17/64 (2006.01)
A61B 17/70 (2006.01)
A61B 17/00 (2006.01)

(52) U.S. Cl.
CPC ............ *A61B 17/72* (2013.01); *A61B 17/6466* (2013.01); *A61B 17/7059* (2013.01); *A61B 17/7233* (2013.01); *A61B 17/8052* (2013.01); *A61B 17/7225* (2013.01); *A61B 17/8004* (2013.01); *A61B 2017/00862* (2013.01)

(58) Field of Classification Search
CPC ........... A61B 17/6466; A61B 17/7059; A61B 17/72; A61B 17/7233; A61B 17/8052; A61B 17/8004; A61B 17/7225; A61B 2017/00862
USPC ................................ 606/71, 280–299, 62–68
See application file for complete search history.

(56) References Cited

U.S. PATENT DOCUMENTS

| | | | |
|---|---|---|---|
| 2,414,882 A * | 1/1947 | Longfellow | 606/65 |
| 4,817,591 A * | 4/1989 | Klaue | 606/64 |
| 6,093,188 A * | 7/2000 | Murray | 606/282 |
| 6,270,499 B1 * | 8/2001 | Leu et al. | 606/64 |
| 6,406,478 B1 * | 6/2002 | Kuo | 606/71 |
| 2003/0078583 A1 | 4/2003 | Biedermann et al. | |

(Continued)

FOREIGN PATENT DOCUMENTS

| | | |
|---|---|---|
| CN | 1668252 | 9/2005 |
| JP | 2002-528162 | 9/2002 |

(Continued)

*Primary Examiner* — Zade Coley
(74) *Attorney, Agent, or Firm* — Fay Kaplun & Marcin, LLP

(57) ABSTRACT

A device for bone fixation defining at least one through hole extending therethrough, the through hole including first and second through apertures separated from one another by a first resilient element deformable radially outward from the first aperture to expand the first aperture and contract the second aperture, the second aperture being sized and shaped to receive therein a bone fixation element, the second through aperture being smaller in size than the first through aperture, a periphery of the first through aperture comprising at least two substantially circular arcs B1 and B2 with respective radii R1 and R2 and respective centers Z1 and Z2 located at a distance X≥0 extending transversely to the resilient element whereby the ratio R1:R2 is in the range between 0.5 and 2.0.

1 Claim, 8 Drawing Sheets

(56) References Cited

U.S. PATENT DOCUMENTS

| | | | |
|---|---|---|---|
| 2004/0073218 A1* | 4/2004 | Dahners | 606/69 |
| 2004/0127904 A1* | 7/2004 | Konieczynski et al. | 606/70 |
| 2005/0004574 A1 | 1/2005 | Muckter | |
| 2005/0090825 A1* | 4/2005 | Pfefferle et al. | 606/69 |
| 2005/0096657 A1* | 5/2005 | Autericque et al. | 606/69 |

FOREIGN PATENT DOCUMENTS

| | | |
|---|---|---|
| JP | 2003-126108 | 10/2002 |
| JP | 2005-40586 | 2/2005 |
| JP | 2005-118603 | 5/2005 |
| WO | 00/24325 | 5/2000 |
| WO | 2004/028383 | 4/2004 |

* cited by examiner

DEVICE FOR BONE FIXATION WITH AT LEAST ONE THROUGH HOLE

FIELD OF INVENTION

The invention relates to a device for bone fixation with at least one through hole for receiving a bone fixation means, whereby the at least one through hole comprises at least two through apertures disposed in a manner that a resilient element is formed between these two apertures.

BACKGROUND INFORMATION

Such devices, i.e. intramedullary nails, bone plates, clamping jaws for external fixation devices or intervertebral implants show the problem that there is always a clearance between the through hole and the bone fixation means inserted therein (e.g. locking elements in case of intramedullary nails or bone screws in case of bone plates). In case of an intramedullary nail the locking bolt is loosely guided within the intramedullary nail but not axially fixed. In the axial direction the bolt is neither guided nor fixed.

For example from U.S. Pat. No. 6,296,645 HOVER ET AL. a hollow intramedullary nail made of metal is known which is provided with one or two synthetic inserts in the diametrally arranged shell apertures of the transverse bore holes, the so called windows, where a locking screw may be inserted. This known intramedullary nail shows the disadvantage that the window-like synthetic inserts may be easily busted, therewith loosening the desired function. Even in case of a very cautious manipulation the two synthetic inserts may be pressed out of their "window" upon insertion of the locking screw whereby the inserts may lose their function.

SUMMARY OF INVENTION

The present invention relates to a device, e.g., an intramedullary nail, a bone plate or a spinal implant which permits an exact positioning and fastening of the bone fragments concerned by means of effective riskless fastenable bone fixation means.

According to an exemplary embodiment of the present invention, a device for bone fixation has at least one through hole for receiving a bone fixation means, whereby the at least one through hole comprises at least two through apertures disposed in a manner that a resilient element is formed between these two apertures. Said resilient element may be pressed outwardly in the direction of the second through aperture when seen from the inside of the first through aperture, such that the first through aperture which is configured to receive a bone fixation means is enlargeable in size and the second through aperture is reducible in size. The periphery of the first through aperture comprises at least two circular arcs B1 and B2 with the respective radii R1 and R2 and with the respective centres Z1 and Z2 located at a distance X≥0 extending transversely to the resilient element (7) whereby the ratio R1:R2 is in the range between 0.5 and 2.0.

Some of the advantages of the present invention are listed below:

a) In case of using a bone fixation means, e.g. a locking bolt having a diameter greater than the one of the through hole the bone fixation means may be clamped through elastic deformation of a region of the device therewith achieving an angular and axial stable connection between the device and the bone fixation means such achieving a better anchorage of the nail in the bone, so that a exact positioning and fastening of the bone fragments taken hold of is permitted;

b) In case of devices having a diminished dimension relative to the through hole (e.g. intramedullary nails with a small nail diameter) bone fixation means (e.g. locking bolts for intramedullary nails) having a larger diameter may be used thanks to the elasticity in the region of the through hole. In case of common intramedullary nails this would cause a weakening of the cross-section of the intramedullary nail because of the too large through holes;

c) Harmful concentrations of stress may be reduced by means of the elasticity in the region of the through holes;

d) The bone fixation means is being clamped in the through hole such as to be secured with regard to all degrees of freedom;

e) The bone fixation means cannot move in axial direction by means of the bracing in the device (securing against "push-out");

f) A screw retention is achieved by means of the bracing; and g) The complete bone fixation (locking in case of intramedullary nails) may be effected from one single side for all possible types of applications.

In a preferred embodiment the ratio R1:R2 of the radii R1 and R2 of the partial circular arcs B1 and B2, which limit the cross-section of the first through aperture at least partially, is in the range of 0.8 and 1.2. Particularly, the radius R1 of the first partial circular arc B1 may be equal to the radius R2 of the second partial circular arc B2 permitting a close fitting of the locking element inserted in the first through aperture at the walls of the first through aperture on the whole arc length B1;B2.

In another embodiment the centres Z1 and Z2 of the two circular arcs B1 and B2 are located in the interior of the first through aperture, whereby the distance A between Z1 and Z2 is different from zero. This permits the advantage that the diameter measured transverse to the longitudinal axis of the first through aperture may be equal or greater than the diameter of the locking element while the length of the first through aperture measured parallel to the longitudinal axis may be smaller than the diameter of the locking element such that upon insertion of the locking element the first through aperture is enlarged in the region of the circular arc B2 next to the second through aperture.

In a further embodiment the through hole is shaped such that the two through apertures do not overlap. Therewith a resilient element may be configured which is attached at its both ends permitting higher loads than a resilient element being attached only at one end.

In yet a further embodiment the through hole comprises three through apertures being arranged axially sequentially and which do not overlap. The two regions between the three through apertures form two resilient elements being diametrally arranged. The advantage of this embodiment is essentially to be seen in the fact that the elastic force is distributed on two resilient elements therewith permitting a reduced load on each resilient member. Peaks of stress may be reduced through the proximal load relieving hole.

In another embodiment the through apertures differ at least partially from a circular geometry.

In another embodiment the first through aperture is connected with one or more second through apertures by means of at least one slot therewith permitting an enhanced elasticity of the resilient elements.

In again another embodiment one or more second through apertures are shaped as slots having a slot width $X_1$ and being convexly curved toward the first through aperture. This permits the configuration of an optimal resilient member for clamping the bone fixation means.

In a further embodiment the first through aperture is provided with two radial bulges having a central angle between 60° and 120°, preferably between 80° and 100°. The second through aperture is located next to the two bulges.

In yet a further embodiment the first through aperture is shaped as circular like, concave or convex figure the concavity or convexity of which extends over a central angle of at least 20° while the second through aperture is located next to the concavity or convexity respectively.

Preferably, the resilient element extends over the entire height of the through hole.

In one embodiment the device is configured as a intramedullary nail, whereby this intramedullary nail is provided with at least one through hole extending transversely to its longitudinal axis and being apt of insertion of bone fixation means on the form of locking element. The intramedullary nail may be hollow, preferably through hollow in the direction of its longitudinal axis.

In another embodiment the through hole is located in that half of the intramedullary nail which is next to the nail tip, such that the first through aperture is located closer to the nail end and the second through hole is located closer to the nail tip. This permits the advantage that a load applied onto the nail must not be absorbed by the resilient element.

In yet another embodiment the through hole is located in that half of the intramedullary nail which is next to the nail end, such that the first through aperture is located closer to the nail tip and the second through aperture is located closer to the nail end. In case of this embodiment which is rotated about 180° relative to the above geometry the load acting on the intramedullary nail is partially absorbed through the resilient element. This arrangement permits the absorption of peaks of stress.

In another embodiment the first through aperture has a maximum diameter $D_B$ measured orthogonally to the longitudinal axis while the thickness BF of the resilient element amounts to preferably 0.05 to 1.00 times the diameter $D_B$. The locking element has a defined diameter $D_V$ which is greater than the length L of the first through aperture measured parallel to the longitudinal axis. Preferably the diameter $D_V$ of the locking element amounts to 1.1 preferably 1.2 times the length L.

The locking element is preferably inserted into the first through aperture of the through hole such that the resilient element is pressed outwardly. The width of the slot $X_1$ is greater than $(D_V-L)$.

Furthermore, the device according to the invention may be configured as bone plate, clamping jaw in case of an external fixation device or as spinal implant.

BRIEF DESCRIPTION OF DRAWINGS

The invention and additional configurations of the invention are explained in even more detail with reference to the partially schematic illustrations of several embodiments. In the drawings.

DETAILED DESCRIPTION

Figure 2:
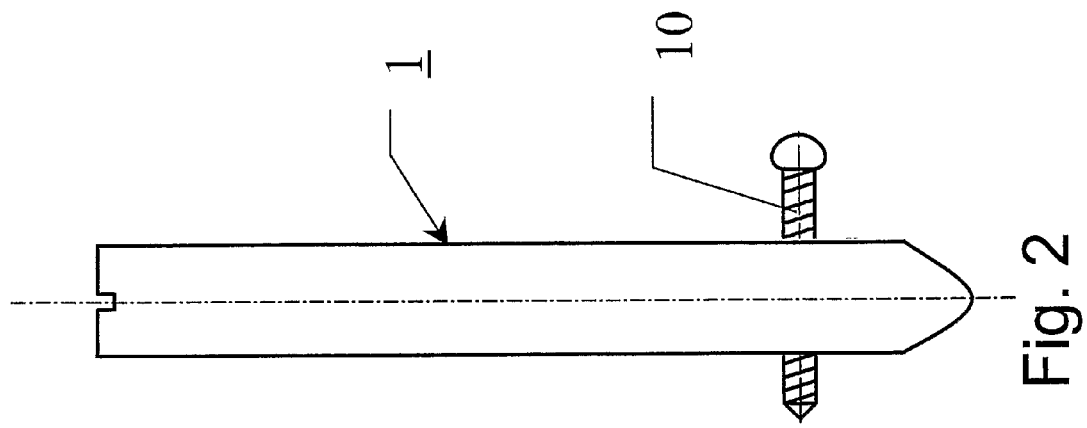
FIG. 2 shows a lateral view turned by 90° on the embodiment according to FIG. 1.
Figure 1:
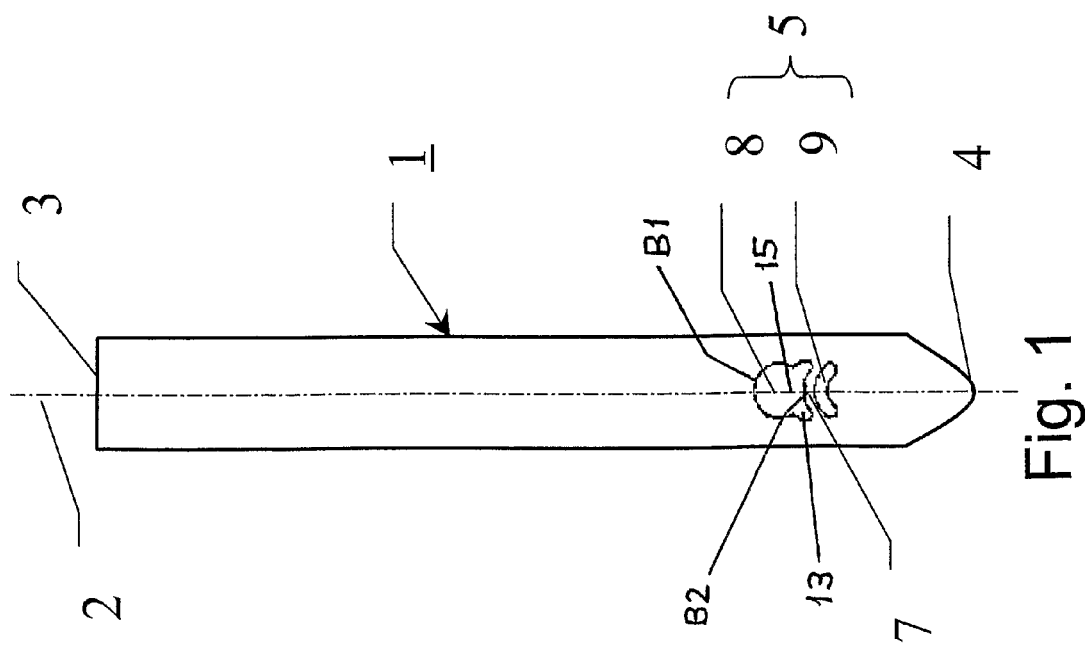
FIG. 1 shows a schematic lateral view to a device according to the invention in the form of an intramedullary nail.

FIG. 1 shows an intramedullary nail 1 with a longitudinal axis 2, a nail end 3, a nail tip 4 and a through hole 5 arranged in the nail half extending towards the nail tip 4 and penetrating the intramedullary nail 1 transversely to the longitudinal axis 2. The through hole 5 comprises a larger first through aperture 8 for insertion of a bone fixation means and a smaller second through aperture 9 whereby the first and second through apertures 8;9 are arranged in an axially sequential manner, the second through aperture 9 being disposed between the first through aperture 8 and the nail tip 4. Furthermore, the first and second through apertures 8;9 are configured symmetrically to an axis of symmetry 15 which coincides with the longitudinal axis 2 of the intramedullary nail 1. The region being axially between the two through apertures 8;9 has a thickness measured parallel to the longitudinal axis 2 dimensioned such that this region is apt to act as a resilient element 7. This resilient element 7 is shaped convexely with respect to the first through aperture 8 and is limited through the first and second through apertures 8;9. The first through aperture 8 is provided with two radial bulges 13 when seen in a cross section orthogonal to the longitudinal axis whereby the bulges 13 are arranged next to the second through aperture 9 and enclose a central angle of 100°. The bulges 13 enlarge the first through aperture 9 permitting a width of the resilient element 7 transversely to the longitudinal axis 2 which is suitable regarding the elasticity of the resilient element 7. As shown in FIG. 2 the first through aperture 8 permits the insertion of a locking element 10, e.g. a locking screw through the intramedullary nail 1 transversely to the longitudinal axis 2. The second through aperture 9 has the shape of a circular ring arc when seen in a cross-section orthogonal to the longitudinal axis 2 whereby the circular ring are is convexely curved towards the first through hole 8.

Figure 3:
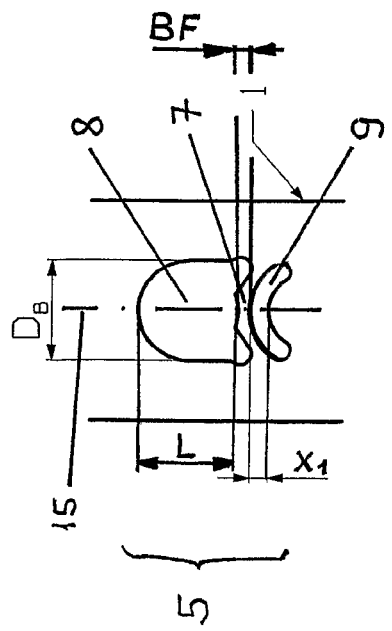
FIG. 3 shows a magnified view of the through hole in the intramedullary nail according to FIG. 1.
Figure 4:
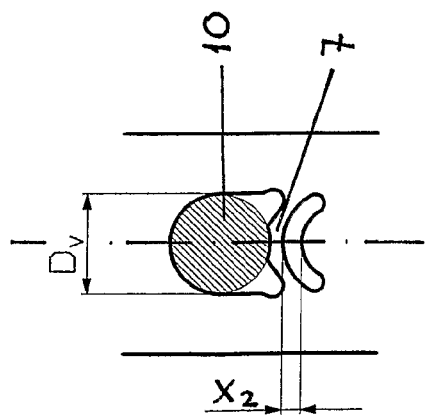
FIG. 4 shows a magnified view of the through hole in the intramedullary nail according to FIG. 1 with a locking element being inserted.

FIGS. 3 and 4 depict the through hole 5 according to the embodiment shown in FIG. 1 in a magnified view. The first through aperture 8 has a length L measured parallel to the longitudinal axis 2 and a maximum diameter $D_B$ measured orthogonally to the longitudinal axis 2, whereby the length L is smaller than the diameter $D_V$ of the locking element 10 (FIG. 4).

The resilient element 7 has a thickness BF measured parallel to the longitudinal axis 2. Furthermore, in an unloaded state of the resilient element 7 the second through aperture 9 formed as a circular ring arc has a slot width $X_1$ measured parallel to the longitudinal axis 1, whereby the slot width $X_1$ is larger than the difference between the diameter $D_V$ and the length L. Upon insertion of the locking element 10 (FIG. 4) the resilient element 7 is deformed such that the slot width $X_2$ is smaller than $X_1$ and since the slot width $X_1$ is larger than the difference between diameter $D_V$ and the length L the slot width $X_2$ is greater than zero.

Figure 5:
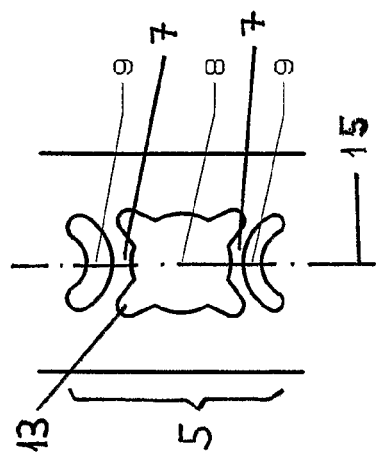
FIG. 5 shows a magnified view of a first variant of a through hole for a device according to the invention.
Figure 6:
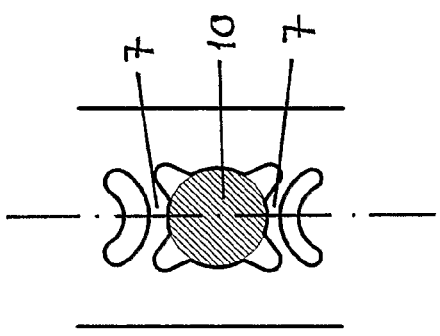
FIG. 6 shows the view according to FIG. 5 with a bone fixation means being inserted in the through hole.

The embodiment of the through hole 5 shown in FIGS. 5 and 6 differs from the embodiment shown in FIGS. 3 and 4 only therein, that it comprises three through apertures 9;8;9 which do not overlap and that the first through aperture 8 is provided with four radial bulges 13 when seen in a cross-section orthogonal to the longitudinal axis 2. The bulges 13 are arranged in pairs each pair being next to the second through apertures 9 and each pair of bulges 13 enclosing a central angle of 100°. A resilient element 7 is formed each between the second through apertures 9 and the central first through aperture 8. The second through aperture 9 disposed between the nail end 3 (FIG. 1) and the central first through aperture 8 is arranged as a mirror image with regard to the second through aperture 9 disposed between the nail tip 4 (FIG. 1) and the first through aperture 8 and with regard to plane of symmetry being orthogonal to the longitudinal axis 2 and penetrating the first through aperture 8.

Figure 7:
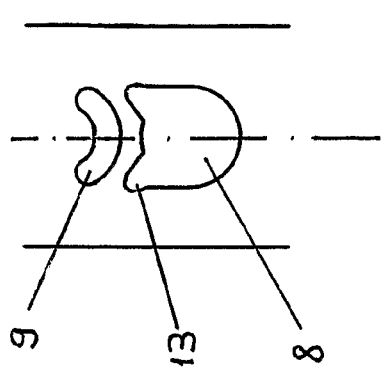
FIG. 7 shows a magnified view of a second variant of the through hole for a device according to the invention.
Figure 8:
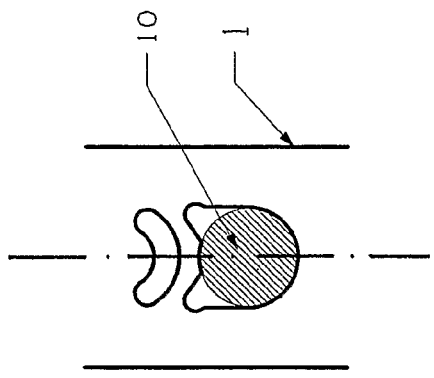
FIG. 8 shows the view according to FIG. 7 with a bone fixation means being inserted in the through hole.

The embodiment of the through hole 5 shown in FIGS. 7 and 8 differs from the embodiment shown in FIGS. 3 and 4 only therein, that the second through aperture 9 is disposed between the nail end 3 (FIG. 1) and that the second through aperture 9 as well as the bulges 13 are disposed as a mirror image with regard to the embodiment shown in FIG. 3 and with regard to a plane of symmetry being perpendicular to the longitudinal axis 2 and penetrating the first through aperture 8.

Figure 9A:
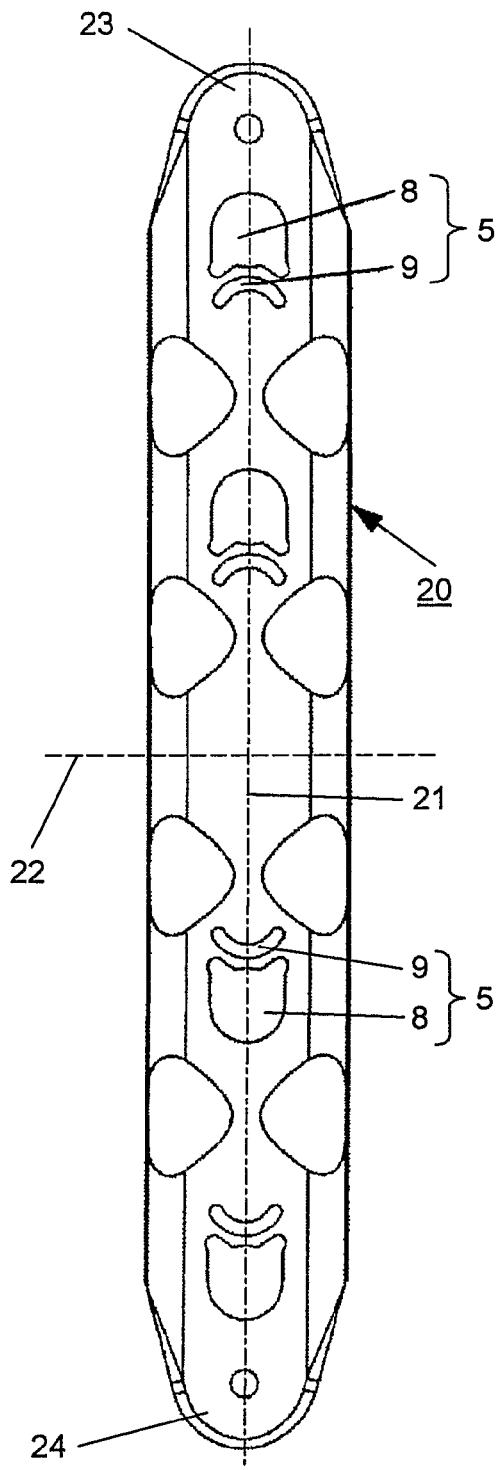
FIG. 9a shows a view (from below) to a device according to the invention in the form of a bone plate whereby the arrangement of the through holes permits an elastic fixation against compression of the bone fragments concerned.
Figure 9B:
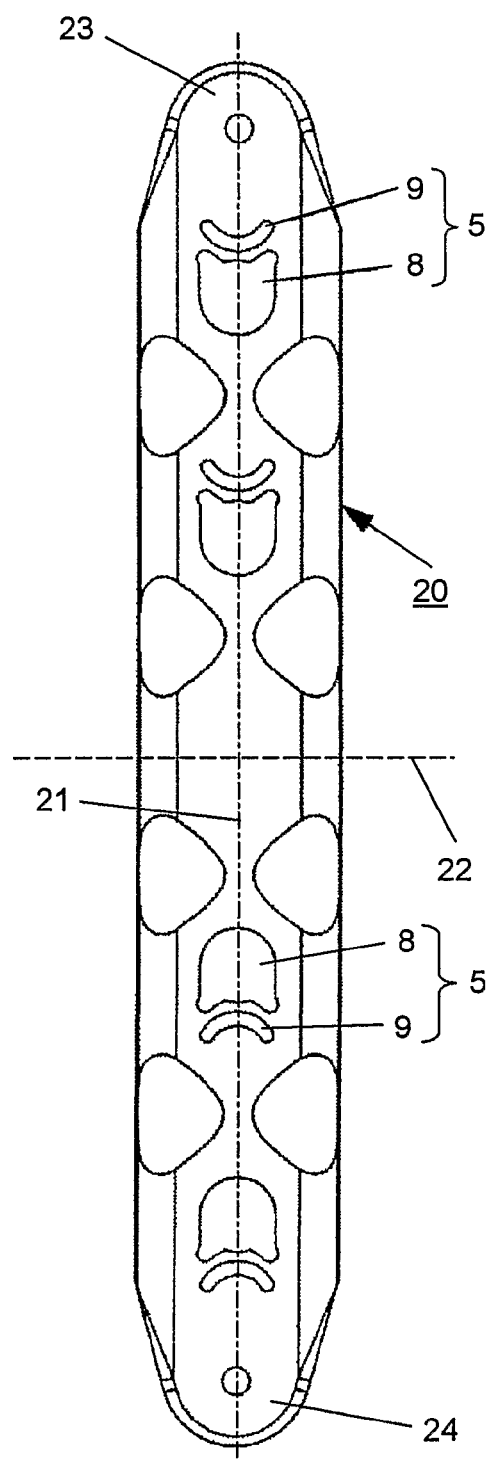
FIG. 9b shows another embodiment of FIG. 9a where the arrangement of the through holes permits a rigid fixation against compression of the bone fragments concerned.

FIGS. 9a and 9b depict another embodiment of the device according to the invention which is configured as a longitudinal bone plate 20 with a central axis 21 and four through holes 5. The through holes 5 are disposed along the central axis 21 whereby the through holes 5 are arranged as mirror images with regard to a plane 22 extending perpendicularly to the central axis 21 and intersecting the bone plate 20 in the middle of its length. The arrangement of the through holes 5 shown in FIG. 9a permits an elastic fixation against compression of the bone fragments concerned. Therefore, each pair of through holes 5 being disposed between one of the two ends 23;24 of the bone plate 20 and the plane 22 is configured in a manner that their first through apertures 8 are disposed towards the respective end 23;24 of the bone plate 20 while their second through apertures 9 are disposed towards the plane 22. The arrangement of the through holes 5 shown in FIG. 9b permits a rigid fixation against compression of the bone fragments concerned. Therefore, each pair of through holes 5 being disposed between one of the two ends 23;24 of the bone plate 20 and the plane 22 is configured in a manner that their first through apertures 8 are disposed towards the plane 22 while their second through holes 9 are disposed towards the respective end 23;24 of the bone plate 20.

Figure 10:
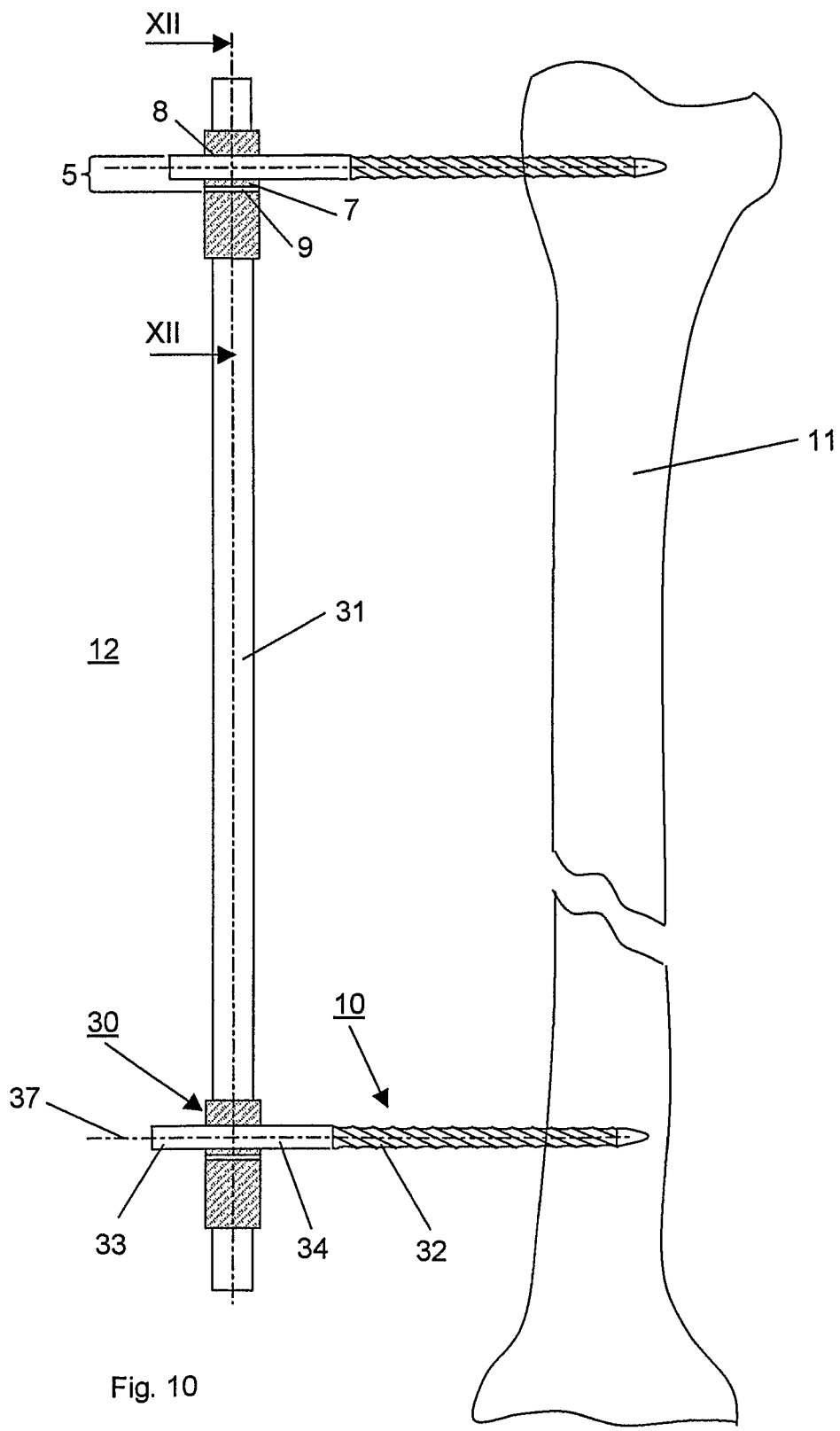
FIG. 10 a longitudinal section through a device according to the invention in the form of a external fixation device with two clamping jaws.

FIG. 10 depicts an external fixation device 12 which is provided with an external longitudinal rod 31 and two clamping jaws 30 being apt to fasten the locking elements 10. The locking means 10 are configured as bone screws 32 and comprise an unthreaded shaft segment 34 extending towards the rear end 33 of the bone screw 32. This shaft segment 34 is being kept in the first through aperture 8 of the through hole 5 by means of the resilient element 7. Upon insertion of the shaft segment 34 into the first through aperture 8 the resilient element 7 is being deformed and partially being pressed into the second through aperture 9.

Figure 11:
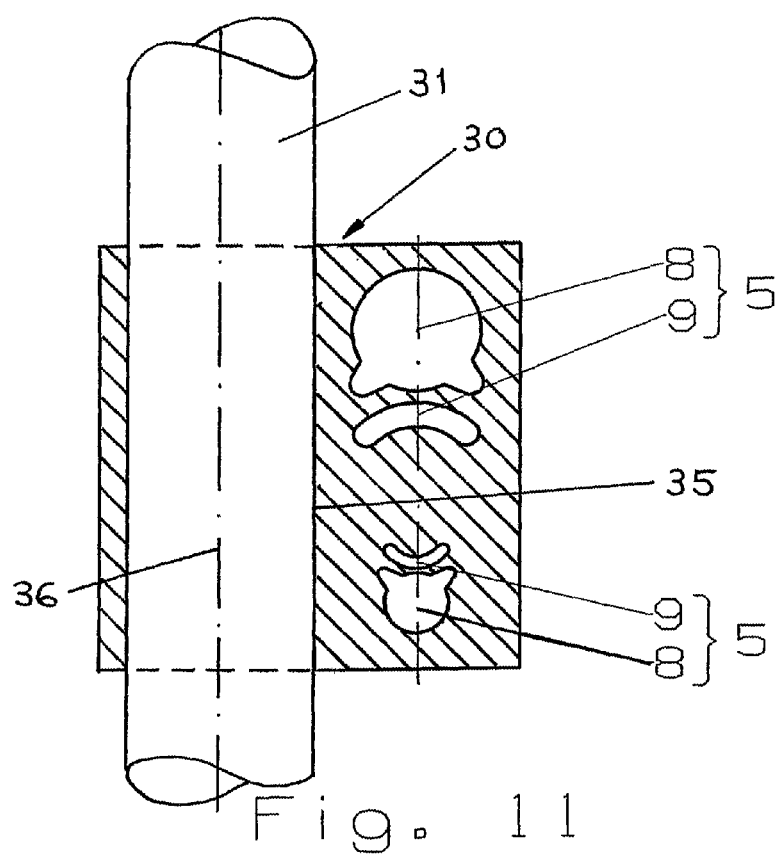
FIG. 11 a longitudinal section through a clamping jaw according to FIG. 10.

The clamping jaws 30 used in case of the external fixation device 12 (FIG. 10) are shown in a longitudinal section in FIG. 11. The clamping jaw 30 comprises an opening 35, which has a central axis 36 being orthogonal to the axes of the screws 37 and which entirely penetrates the clamping jaw 30. The longitudinal rod 31 is inserted parallel to the central axis 36 and is being fixed e.g. with a fastener (not shown) in the clamping jaw 30.

Figure 12:
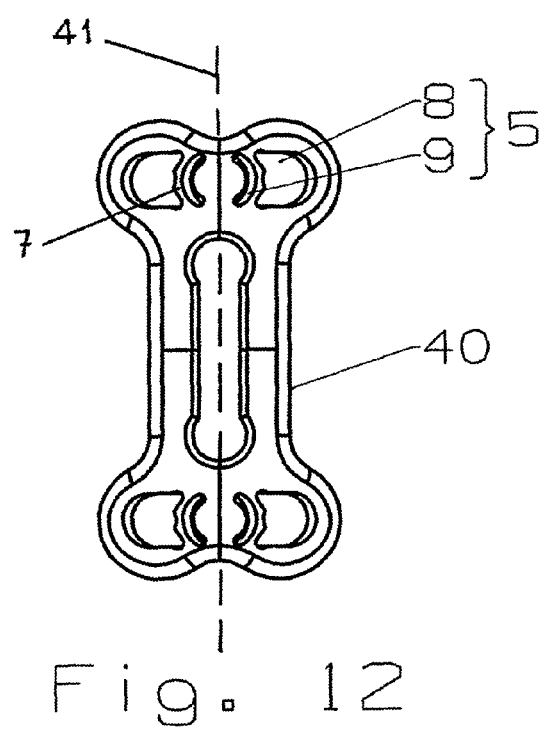
FIG. 12 a top view on a device according to the invention in the form of a vertebral plate.

FIG. 12 depicts a vertebral plate 40 with a plane of symmetry 41 intersecting the vertebral plate 40 in the longitudinal direction and being provided with four through holes 5 according to FIG. 1, whereby each two through holes 5 are symmetrical with regard to the plane of symmetry 41.

Figure 13:
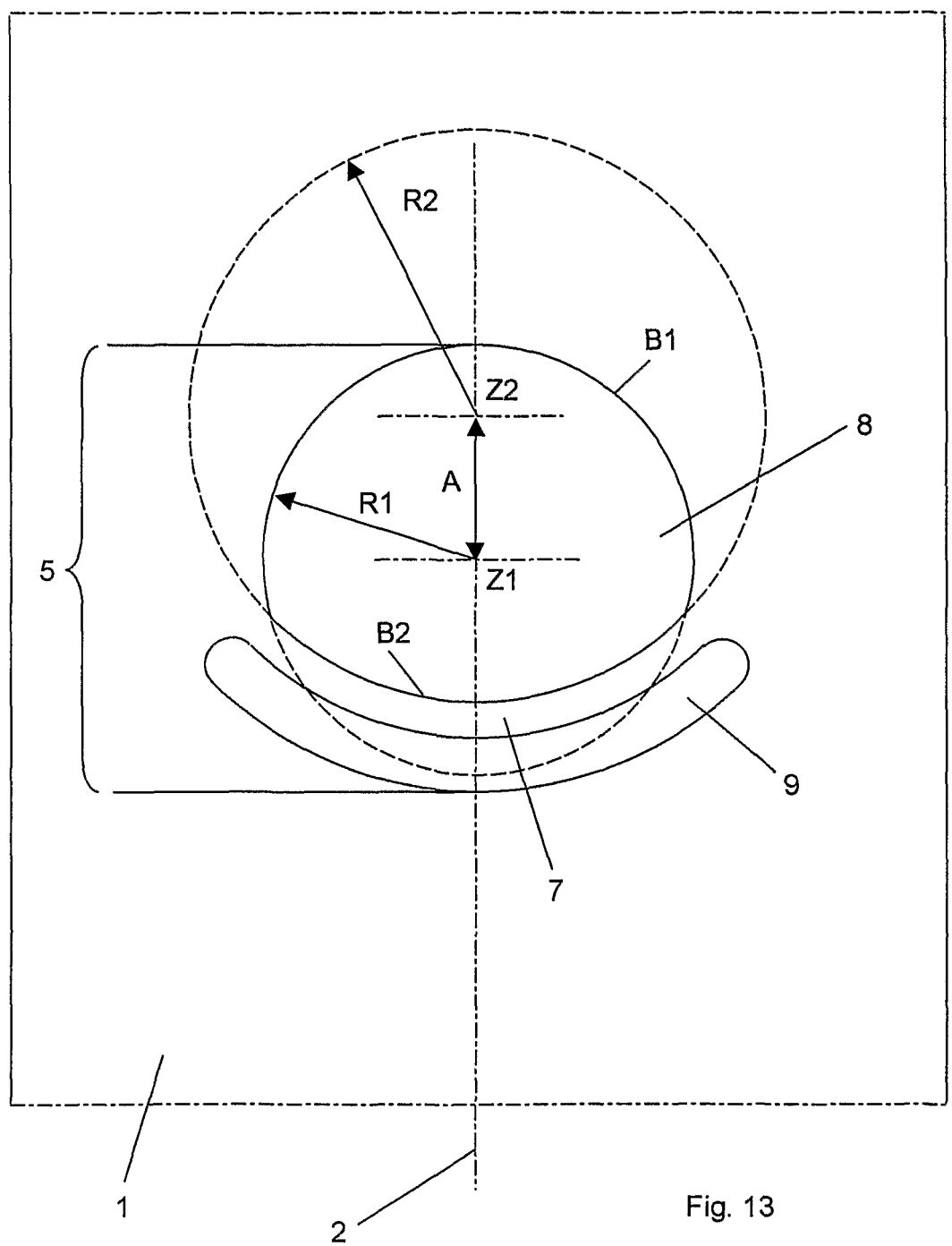
FIG. 13 a schematic view of a third variant of the through hole in a device according to the invention.

FIG. 13 shows a further embodiment of the through hole 5 at the example of the intramedullary nail 1 according to FIG. 1. The through hole 5 is symmetrical with regard to a plane defined through the longitudinal axis 2 of the intramedullary nail 1 and the hole axis (perpendicular to the drawing plane). The first through aperture 9 has a cross-section having a circumference with two different partial circular arcs B1;B2. The radius R1 of the first partial circular arc B1 is smaller than the radius R2 of the second partial circular arc B2. The centers Z1;Z2 of the partial circular arcs B1;B2 are situated on the longitudinal axis 2 of the intramedullary nail 1 and have a mutual distance A, whereby the center Z1 of the first partial circular arc B1 is next to the second through aperture 9. The second through aperture 9 is configured as a partial circular ring arc being concentric with the center Z2.

Figure 14:
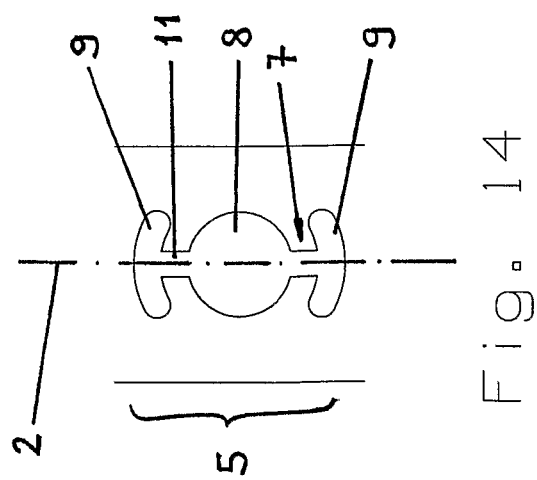
FIG. 14 a magnified view of a fourth variant of the through hole in a device according to the invention.

The embodiment of the through hole 5 shown in FIG. 14 differs from the embodiment shown in FIGS. 3 and 4 only therein, that the through hole 5 comprises three through apertures 9;8;9 which do not overlap whereby the first through aperture 8 is connected with each second through aperture 9 by means of a slot 11 extending parallel to the longitudinal axis 2 of the intramedullary nail 1. Therewith, a two-piece resilient element 7 is formed each between the first through aperture 8 and the two second through apertures 9. The first through aperture 8 is shaped circular when seen in a cross-section orthogonal to the longitudinal axis 2 of the intramedullary nail 1 while the two second through apertures 9 are shaped as partial ring arcs when seen in the aforementioned cross-section, the centers of the radii of curvature of the two partial ring arcs being in the area of the through hole 5.

Figure 15:
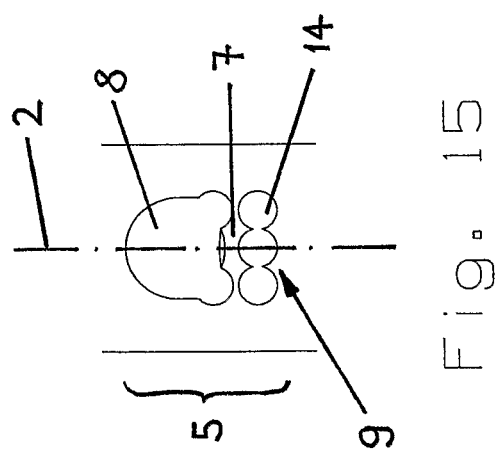
FIG. 15 a magnified view of a fifth variant of the through hole in a device according to the invention.

The embodiment of the through hole 5 shown in FIG. 15 differs from embodiment shown in FIGS. 3 and 4 only therein, that the through hole 5 comprises a second through aperture 9 which is formed through three bore holes 14 being disposed on a straight line extending perpendicular to the longitudinal axis 2 of the intramedullary nail 1 and overlapping each other.

Figure 16:
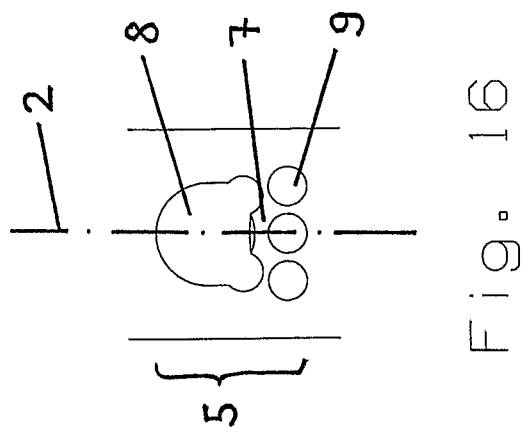
FIG. 16 a magnified view of a sixth variant of the through hole in a device according to the invention.

The embodiment of the through hole 5 shown in FIG. 16 differs from the embodiment shown in FIG. 15 only therein, that the through hole 5 comprises three second through apertures 9 being disposed on a straight line extending perpendicular to the longitudinal axis 2 of the intramedullary nail 1 and which do not overlap each other.

What is claimed is:

1. A device for bone fixation defining at least one through hole extending therethrough, the through hole including first and second through apertures separated from one another by a first resilient element deformable radially outward from the first aperture to expand the first aperture and contract the second aperture, the second aperture being sized and shaped to receive therein a bone fixation element, the second through aperture being smaller in size than the first through aperture, a periphery of the first through aperture comprising at least two substantially circular arcs B1 and B2 with respective radii R1 and R2 and respective centres Z1 and Z2 located at a distance X>0 extending transversely to the resilient element whereby the ratio R1:R2 is in the range between 0.5 and 2.0, wherein the through hole further comprises a third through aperture which does not overlap the first and second apertures, the third through aperture being separated from the first through aperture by a second resilient element deformable radially outward from the first aperture to expand the first aperture and contract the third aperture, the third aperture being sized and shaped to receive therein a bone fixation element.

* * * * *